(12) United States Patent
Schmieding et al.

(10) Patent No.: US 7,879,105 B2
(45) Date of Patent: Feb. 1, 2011

(54) METHOD AND APPARATUS FOR ARTHROSCOPIC JOINT RESURFACING

(75) Inventors: Reinhold Schmieding, Naples, FL (US); Robert Sluss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1087 days.

(21) Appl. No.: 11/283,716

(22) Filed: Nov. 22, 2005

(65) Prior Publication Data
US 2006/0149370 A1    Jul. 6, 2006

Related U.S. Application Data

(60) Provisional application No. 60/630,097, filed on Nov. 23, 2004.

(51) Int. Cl.
*A61F 2/40* (2006.01)
(52) U.S. Cl. ............... 623/19.11; 623/14.12; 623/23.72
(58) Field of Classification Search ............... 623/14.12, 623/23.72, 19.11–19.14; 600/36; 606/232
See application file for complete search history.

(56) References Cited

U.S. PATENT DOCUMENTS 6,024,758 A * 2/2000 Thal ..................... 606/232
6,641,597 B2 * 11/2003 Burkhart et al. ............ 606/232
2005/0267584 A1 * 12/2005 Burdulis et al. .......... 623/20.19

OTHER PUBLICATIONS

Ball, C.M., Galatz, L.M., & Yamaguchi, K. (2001). Meniscal allograft interposition arthroplasty for the arthritic shoulder: description of a new surgical technique Tech shoulder elbow surgery, 2(4):247-254.*

* cited by examiner

*Primary Examiner*—Corrine M McDermott
*Assistant Examiner*—Megan Wolf
(74) *Attorney, Agent, or Firm*—Dickstein Shapiro LLP

(57) ABSTRACT

An arthroscopic method of glenoid resurfacing with a meniscal allograft. The glenohumeral joint is debrided and holes are formed around the anterior and posterior perimeter of the glenoid rim. A meniscal allograft is prepared by removing it from its bone block and then bringing together its two horns to form a ring. Subsequent to the formation of the graft ring, a series of loops are installed along the edge of the graft. The loops correspond to the holes on the glenoid surface. Once the graft has been successfully placed on the glenoid, the loops are positioned in close proximity to the pre-drilled holes. Fixation devices such as anchors may be installed over the loops, to attach the perimeter of the graft to the glenoid through the pre-drilled holes.

5 Claims, 8 Drawing Sheets

METHOD AND APPARATUS FOR ARTHROSCOPIC JOINT RESURFACING

This application claims the benefit of U.S. Provisional Application Ser. No. 60/630,097 filed on Nov. 23, 2004, the disclosure of which is incorporated by reference herein.

BACKGROUND OF THE INVENTION

1. Field of the Invention

The present invention relates to articular joint resurfacing and, more specifically, to an arthroscopic method and apparatus for securing a replacement articular meniscal allograft.

2. Description of the Related Art

Chronically painful arthritic glenohumeral joints that are recalcitrant to non-surgical treatments have been typically treated with open arthroplasty-type procedures. Although these procedures are successful, certain patients may benefit from a less invasive surgical technique, in which a meniscal allograft may be utilized to resurface the glenoid and to decrease the pain and increase the function of the humeral joint in these patients.

SUMMARY OF THE INVENTION

The present invention provides an arthroscopic method of joint resurfacing with a replacement graft to aid in the restoration of function to patients debilitated by arthritic conditions of bearing surfaces in joints. The bearing surfaces in joints may be replaced or resurfaced arthroscopically using a graft secured in place with suture.

In an exemplary embodiment, the present invention provides an arthroscopic method of glenoid resurfacing with a meniscal allograft secured to the glenohumeral joint surface by sutures. To install the meniscal allograft of the present invention, the glenohumeral joint is first examined arthroscopically and debrided of any fibrillated tissue and osteophytes. Once the anterior and posterior rims of the glenoid are clearly defined, holes are formed around the anterior and posterior perimeter of the glenoid rim.

A meniscal allograft is prepared by removing it from its bone block and then bringing together its two horns in an overlapping fashion to form a ring. The horns are attached to each other using a suture, for example. Subsequent to the formation of the graft ring, a series of loops are installed along the edge of the graft. The loops correspond to the holes on the glenoid surface. Additional sutures may be provided as traction sutures on the anterior and posterior side of the graft, to aid in the introduction of the graft into the glenohumeral joint.

Once the graft has been successfully placed on the glenoid, the loops are positioned in close proximity to the pre-drilled holes. Fixation devices such as anchors may be installed over the loops, to attach the perimeter of the graft to the glenoid through the pre-drilled holes.

BRIEF DESCRIPTION OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventors of carrying out their invention. Various modifications, however, will remain readily apparent to those skilled in the art.

Although the present invention will be described below with reference to an exemplary glenoid repair, the invention is not limited to this exemplary embodiment. Accordingly, the structures and techniques of the present invention have applicability to joint repairs generally, and the invention must not be limited to glenoid repairs. Thus, the invention has applicability to any bearing surfaces in joints which are replaced or resurfaced arthroscopically using a graft secured in place with suture.

In an exemplary embodiment, the present invention provides an arthroscopic method of glenoid resurfacing with a meniscal allograft to aid in the restoration of function to patients debilitated by arthritic conditions of the glenohumeral joint. To install the meniscal allograft of the present invention, the glenohumeral joint is first examined arthroscopically and debrided of any fibrillated tissue and osteophytes. Articular cartilage is also removed from the glenoid surface, and the edge of the glenoid adjacent to the labrum is subsequently gently debrided to reveal a bleeding bed. Once the anterior and posterior rims of the glenoid are clearly defined, holes are formed around the anterior and posterior perimeter of the glenoid rim.

Subsequent or prior to, or simultaneously with, the formation of holes around the anterior and posterior perimeter of the glenoid rim, a meniscal allograft is prepared by removing it from its bone block and then bringing together its two horns in an overlapping fashion to form a ring. The horns are attached to each other using fastening devices such as sutures, for example. Subsequent to the formation of the graft ring, a series of loops are provided along the edge of the graft. The loops correspond to the holes on the glenoid surface. Additional sutures may be provided as traction sutures on the anterior and posterior side of the graft, to aid in the introduction of the graft into the glenohumeral joint. Once the graft has been successfully placed on the glenoid, the loops are positioned in close proximity to the pre-drilled holes. Fixation devices such as anchors may be installed over the loops, to attach the graft to the glenoid through the pre-drilled holes.

Figure 1:
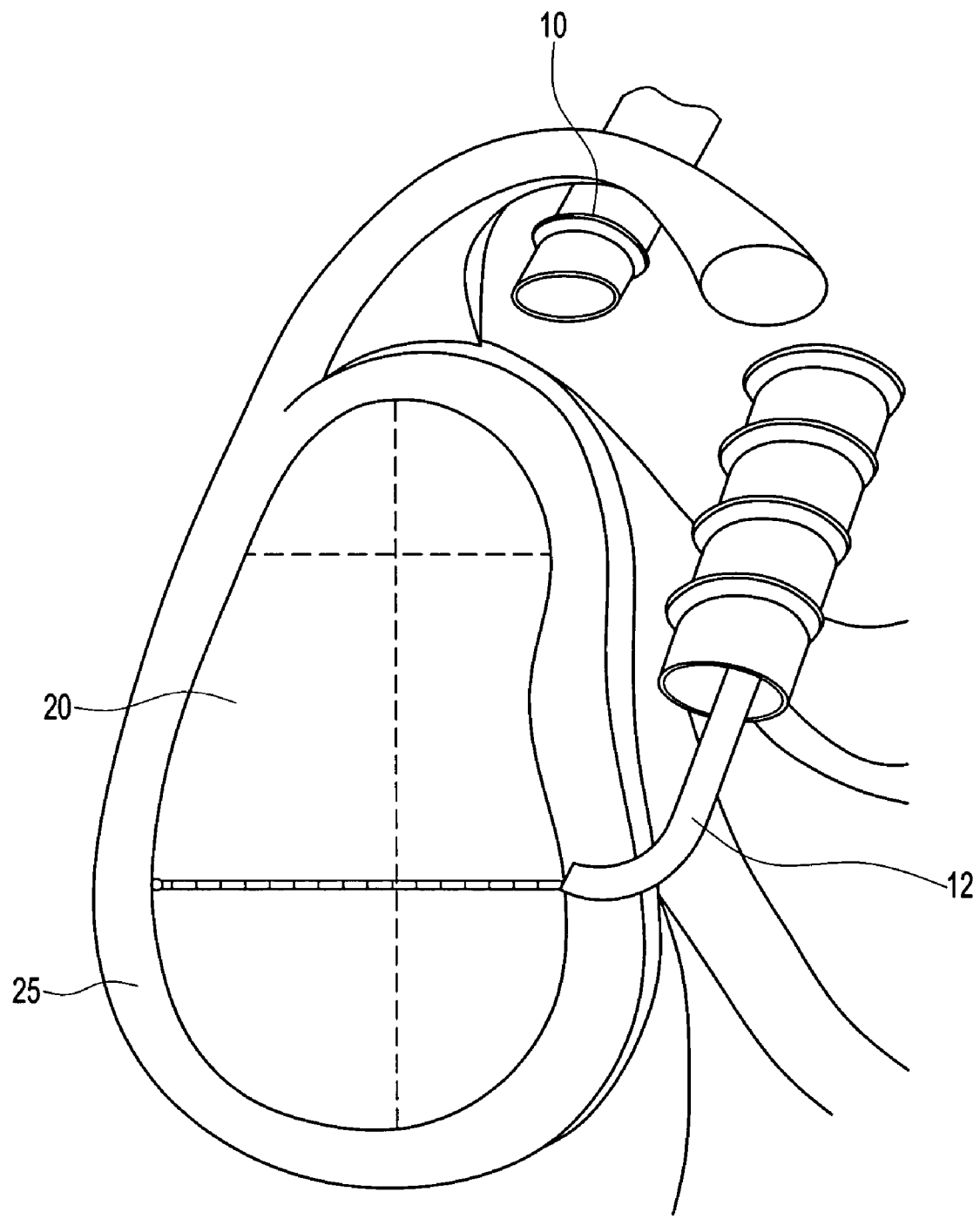
FIG. 1 is a lateral view of a human shoulder with the glenoid undergoing a method of glenoid resurfacing according to the present invention.
Figure 2:
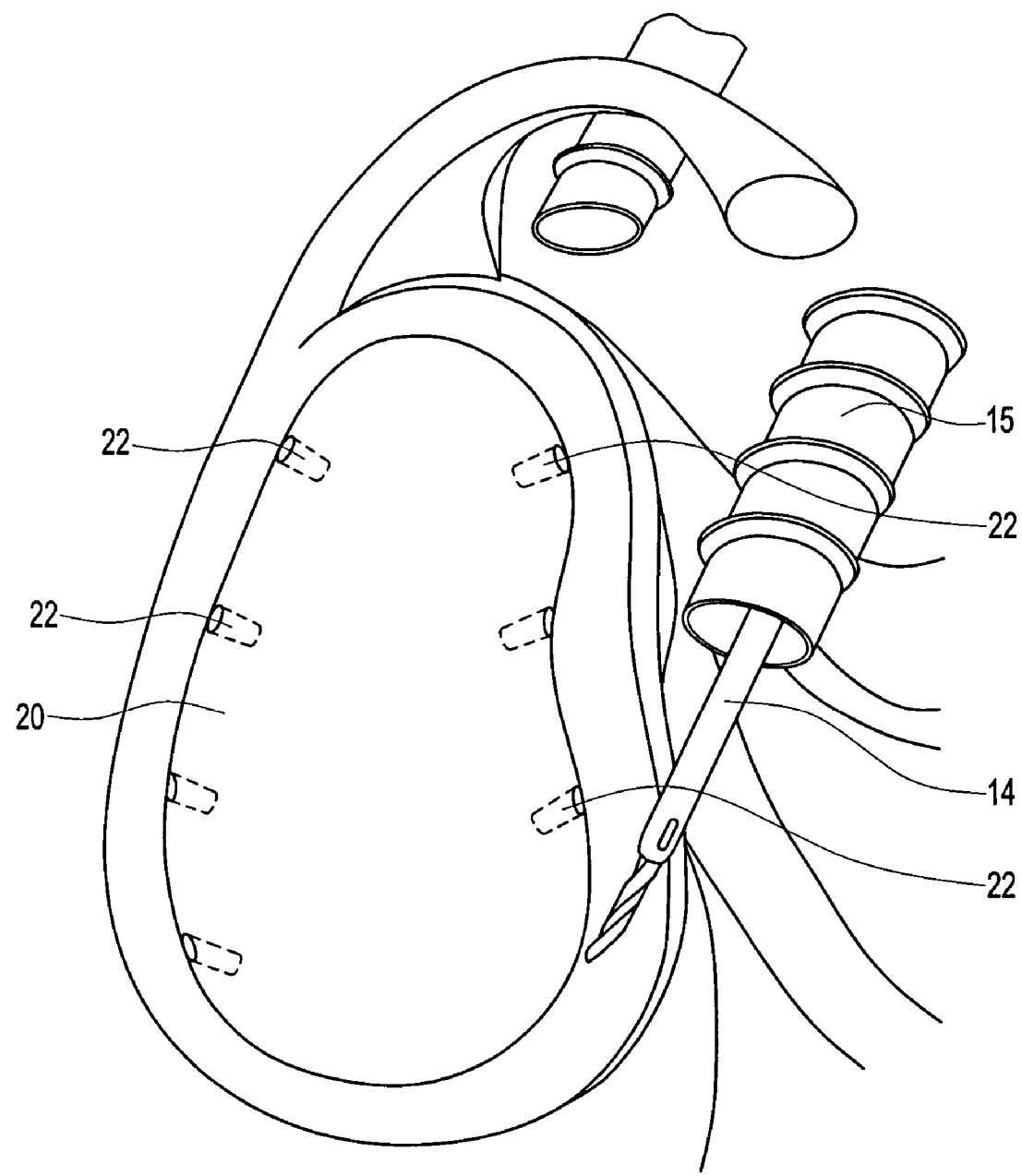
FIG. 2 illustrates the glenoid of FIG. 1 at a preparation stage subsequent to that shown in FIG. 1.
Figure 3:
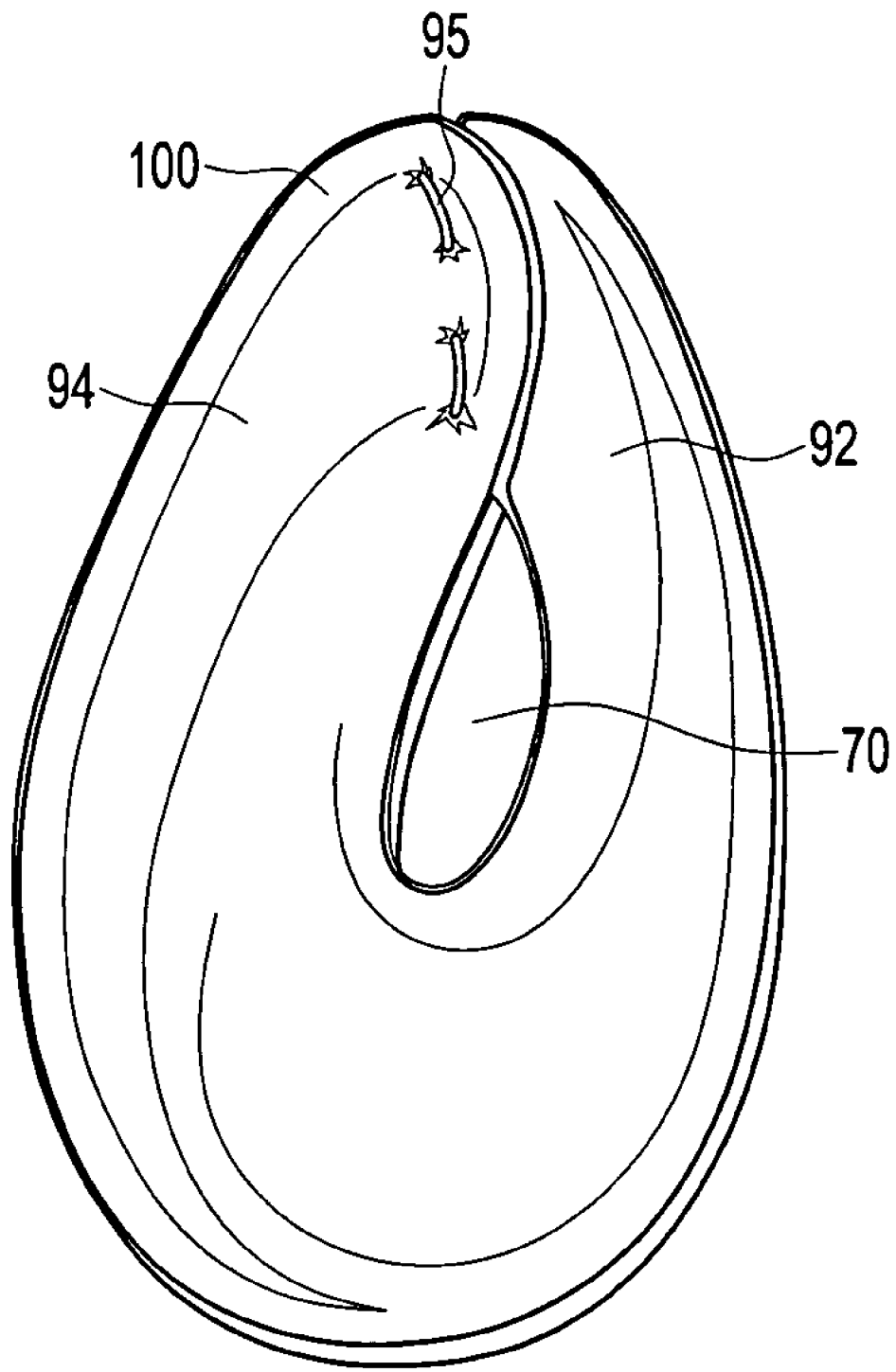
FIG. 3 illustrates a meniscal allograft prepared in accordance with the present invention.
Figure 4:
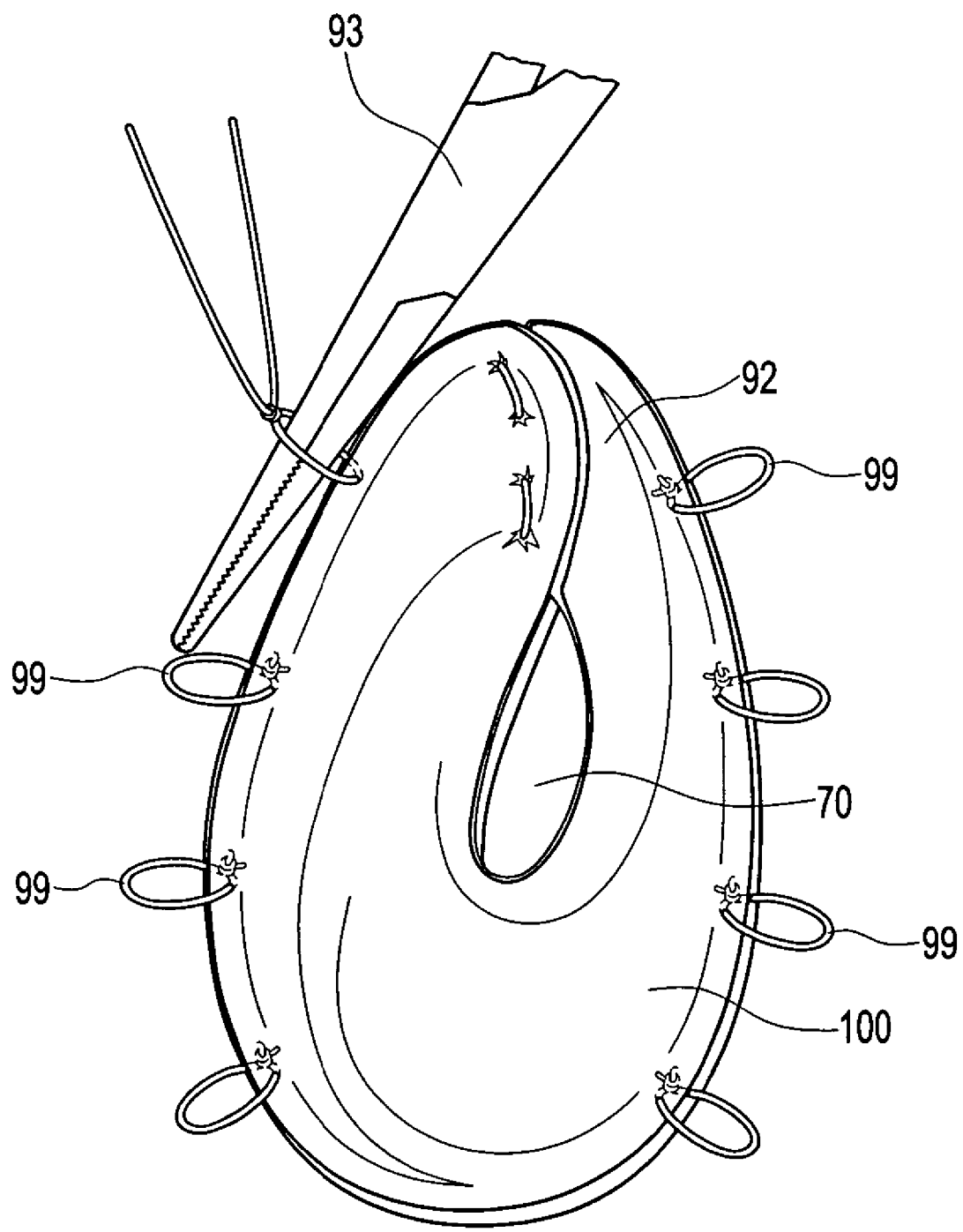
FIG. 4 illustrates the meniscal allograft of FIG. 3 at a preparation stage subsequent to that shown in FIG. 3.
Figure 5:
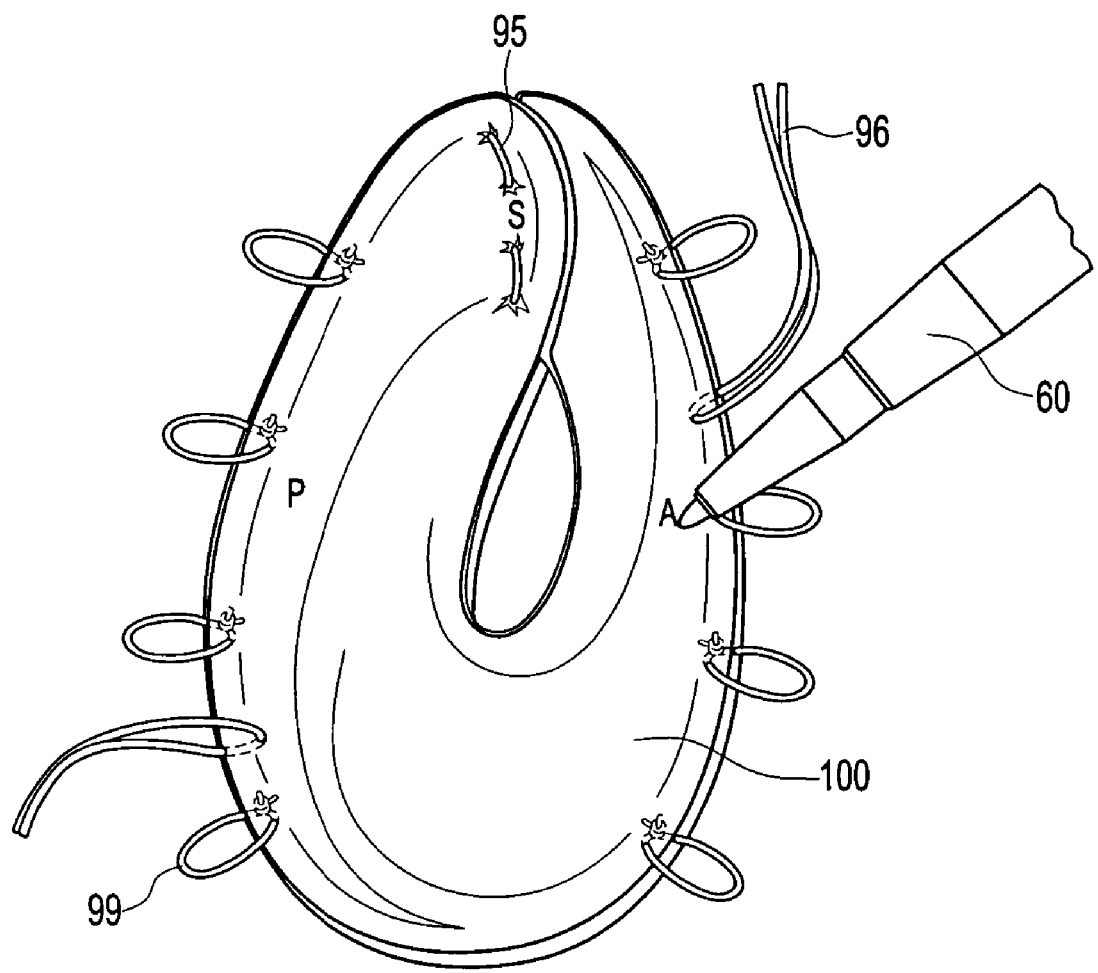
FIG. 5 illustrates the meniscal allograft of FIG. 3 at a preparation stage subsequent to that shown in FIG. 4.
Figure 6:
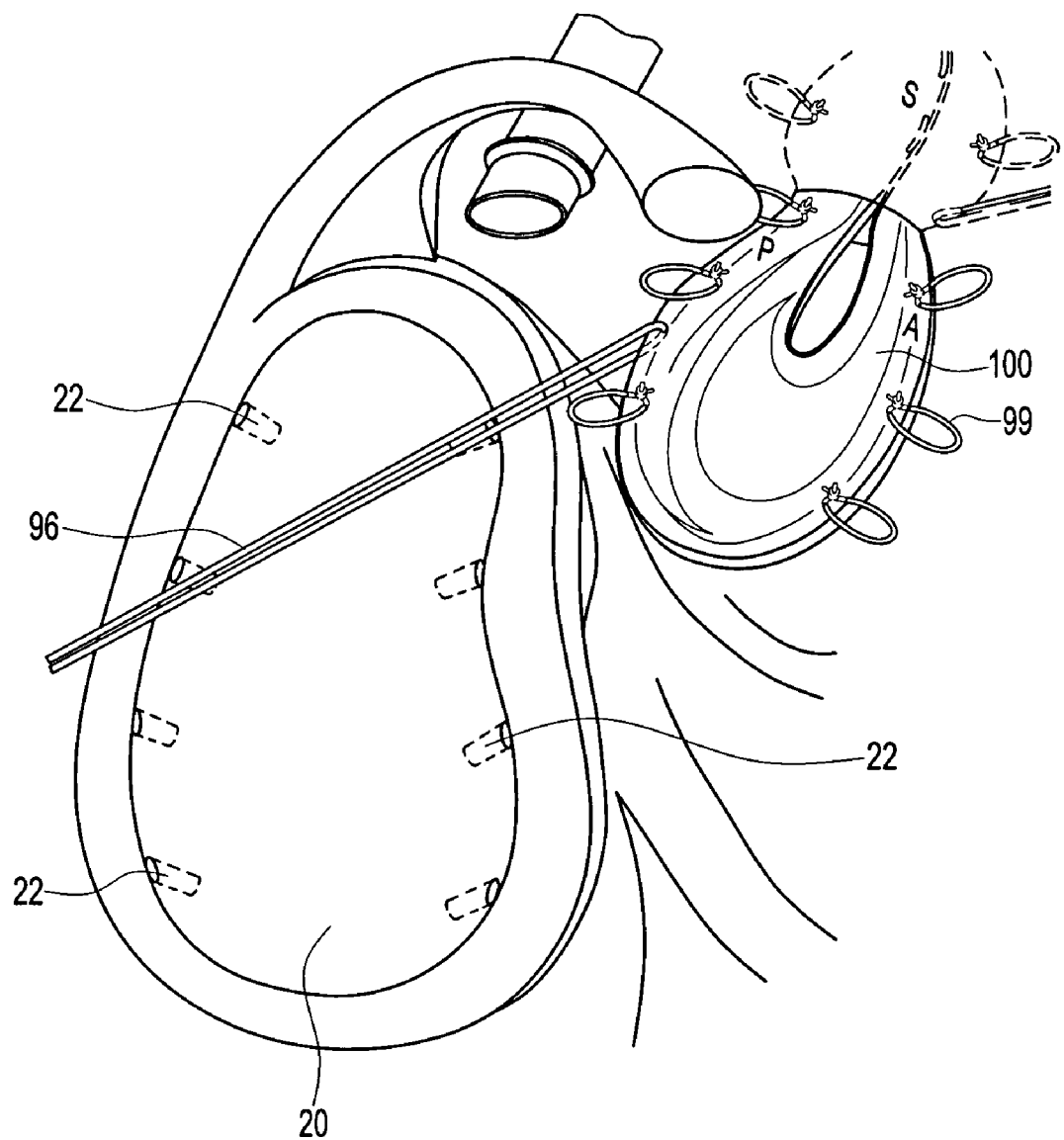
FIG. 6 illustrates the meniscal allograft of FIG. 5 in the proximity of the glenoid of FIG. 2 undergoing a resurfacing technique according to the present invention.
Figure 7:
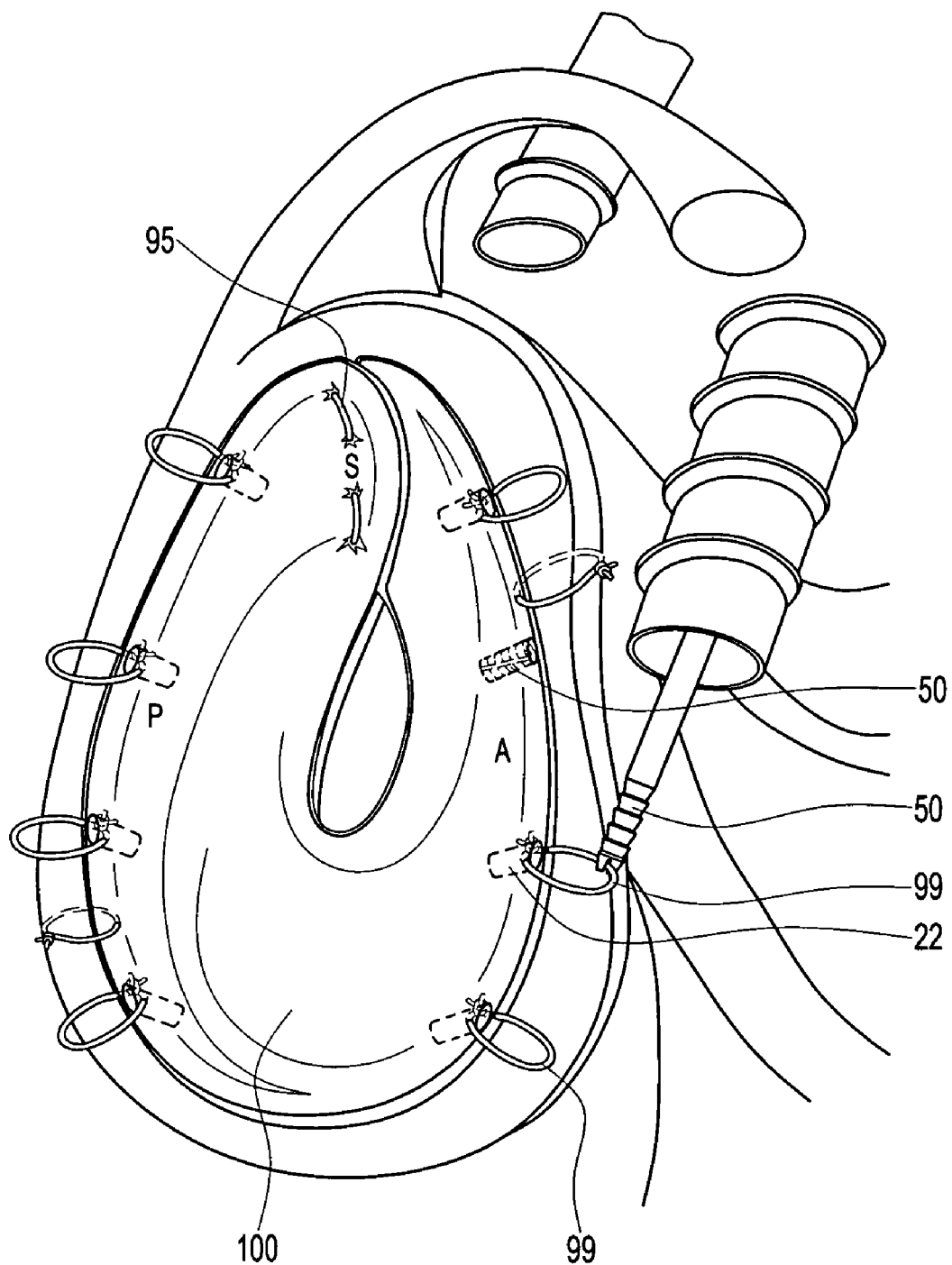
FIG. 7 illustrates the meniscal allograft of FIG. 5 in the proximity of the glenoid of FIG. 2 and at a stage subsequent to that shown in FIG. 6.
Figure 8:
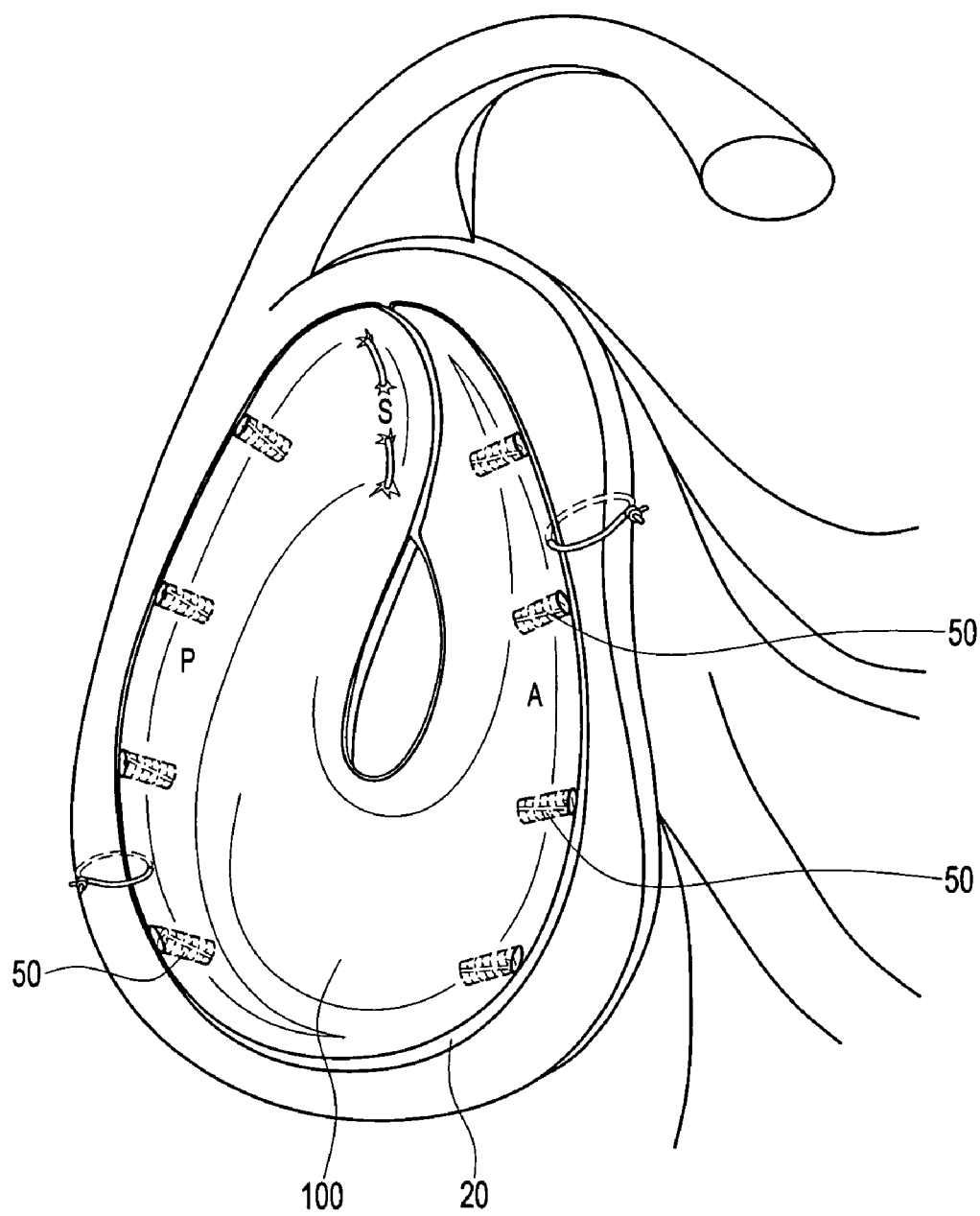
FIG. 8 illustrates the meniscal allograft of FIG. 5 in the proximity of the glenoid of FIG. 2 and at a stage subsequent to that shown in FIG. 7.

Referring now to the drawings, where like elements are designated by like reference numerals, FIGS. 1 and 2 illustrate the preparation of the glenoid before undergoing a method of glenoid resurfacing according to the present invention, while FIGS. 3-5 illustrate the preparation of the graft employed for glenoid resurfacing. FIGS. 6-8 illustrate the method of glenoid resurfacing using the meniscal allograft of FIGS. 3-5 according to the present invention.

Reference is now made to FIGS. 1 and 2, which illustrate the interior of a right human shoulder in a lateral perspective with glenoid 20 and glenoidal labrum 25 that will accommodate a meniscal allograft 100 in accordance with a method of glenoid resurfacing of the present invention.

Prior to the method of graft fixation of the present invention, appropriate radiological studies may be conducted to determine if the humeral head and/or glenoid 20 have advanced patterns of wear that may require procedures alternative or additional to the one of the present invention. For example, excessive glenoid wear or severe humeral head deformity with advanced osteophytic formation may require more aggressive procedures.

The method of glenoid resurfacing of the present invention may be performed in the lateral decubitus or beach chair position. The arthroscope is initially inserted into the glenohumeral joint through a posterior portal. Preferably, this portal is placed 3 cm distal to the posterior corner of the acromion, in a position lateral and inferior to the standard posterior portal of the shoulder. The lateral placement facilitates proper anchor placement into the glenoid rim. The inferior placement allows access to the inferior capsule and labrum as well as the posterior/inferior glenoid rim.

An anterior inferior portal is created with an outside-in technique just superior to the articular fibers of the subscapularis tendon and lateral enough to provide the proper angle for anchor placement into the glenoid rim. A 8.25 mm threaded cannula is placed into this portal. Initial debridement of the joint may be performed with a mechanical shaver through this portal, to enable complete visualization of the glenoid surface.

The glenohumeral joint is examined arthroscopically and debrided of any loose bodies, fibrillated tissue and osteophytes. The labrum is examined and its viability determined. Both the humeral and glenoid surfaces are examined and the severity of cartilaginous loss is recorded.

Once the complete visualization of the glenoid is established, the glenoid dimensions are measured using arthroscopic measuring probes. Preferably, three measurements may be conducted, including total glenoid height, superior ⅓ width and the widest point. As shown in FIG. 1, two measuring probes are utilized. The straight probe (which would be introduced through cannula 10 of FIG. 1) is utilized to obtain the anterior to posterior width of the glenoid at the superior ⅓ of the glenoid and at the widest point. The right angle measuring probe 12 is utilized through the anterior portal to obtain superior to inferior measurements (the total glenoid height).

Alternatively, an antero-superior portal may be created with an outside-in technique. This portal may be utilized for visualization during the procedure. The straight measuring probe may be utilized to obtain the glenoid height through this portal prior to switching the arthroscope to this position. After all measurements are obtained, the results may be recorded and the arthroscope placed through the antero-superior portal, so that another 8.25 mm threaded cannula is placed in the posterior portal.

Preparation of the glenoid surface is conducted by removing any remaining articular cartilage using a combination of a rasp, curette and mechanical burr, for example. The bony surface around the edge of the glenoid adjacent to the labrum is then gently debrided to reveal a bleeding bed. Care is taken to preserve any labral tissue that remains, as it will be utilized to assist in fixation of the allograft in the procedure.

Once the anterior and posterior rims of the glenoid are defined, holes 22 (FIG. 2) are formed around the perimeter of the glenoid 20 using a drill 14 and a guide 15 (FIG. 2), for example, a V-Tak drill and a Bio-SutureTak drill guide, both sold by Arthrex, Inc. of Naples, Fla. Holes 22 are placed around the anterior and posterior perimeter of the glenoid rim just as they would be placed in a labral repair immediately adjacent to the glenoid face. The orientation of the longitudinal axis of the holes relative to the longitudinal axis of the glenoid 20 may vary, depending on the characteristics of the glenoid, such as the size and configuration, as well as the accessibility to the glenoid by the surgeon manipulating the drill 14. Thus, the holes 22 may have a parallel orientation relative to each other, or alternatively, may be orientated at various angles with respect to each other.

In an exemplary embodiment, and as shown in FIG. 2, drill holes 22 are placed four anterior and four posterior, and equally spaced from each other. Thus, although FIG. 2 shows the formation of eight holes drilled within the glenoid 20, the invention is not limited to this exemplary embodiment, and contemplates the formation of any number of holes within the glenoid rim with any configuration and orientation, depending upon the configuration of the glenoid and of the repair site, as well as the configuration of the drilling instrument and of the meniscal allograft to be subsequently attached. For example, and in accordance with another exemplary embodiment of the present invention, the holes may be placed five to six anterior and four to five posterior, and may be equally spaced at clock points corresponding to 1, 2, 3, 4, 5, 6, 7, 8, 9, 10 and 11 o'clock positions. In any event, care must be taken to ensure that an adequate bone bridge remains between all drilled holes. An accessory portal with a stab incision may be performed in the posterior superior position, immediately adjacent to the posterior corner of the acromion, to allow placement of the drill holes 22 in the 10 and 11 o'clock positions.

Subsequent to the formation of the holes 22 and prior to meniscal graft introduction, capsular release could be performed circumferentially, to help increase motion that is usually compromised in the arthritic shoulder.

Reference is now made to FIGS. 3-5 which illustrate the preparation of meniscal allograft 100 of the present invention. Preparation of the meniscal allograft may be conducted simultaneously with the arthroscopic preparation of the glenoid, or at different times. A cadaveric lateral meniscal allograft is the preferred soft tissue for transportation, as it provides appropriate anatomic surface covering while being small enough to allow ease with arthroscopic insertion. The meniscus is removed from its bone block and any fibrillated tissue around horns 92, 94 (FIG. 3) is removed using a scalpel or small curved Mayo scissor, for example. The two horns 92, 94 are brought together in an overlapping fashion to form a ring 70, as shown in FIGS. 3-5. The dimensions of the ring 70 are adjusted until the dimensions of the graft closely match the dimensions of the glenoid. The horns 92, 94 are attached to each other using a series of sutures 95, for example #0 FiberWire™ suture (sold by Arthrex, Inc. of Naples, Fla.), placed so that the complete edge of each horn is securely attached to the other horn and the knots are on the undersurface of the graft nearest to the glenoid surface (FIG. 3).

Subsequent to the formation of the initial graft ring, a series of loops 99 (FIG. 4), for example suture loops, are installed along the edge of the graft 100 that will correspond to the holes 22 on the glenoid surface. The loops 99 preferably include multiple loops of a high strength suture. Exemplary high strength suture materials include, without limitation, those that are based on polyethylene. These suture materials typically contain filaments, fibers, or threads made in whole or in part from a polyethylene. A preferred example of a high strength suture is FiberWire™ suture, sold by Arthrex, Inc. of Naples, Fla., and described in U.S. Pat. No. 6,716,234, the disclosure of which is incorporated herein by reference.

Loops 99 can be formed by joining two ends of the suture, for example. The ends can be joined using knot-tying, for example. Other methods of forming loops and joining suture are contemplated by this invention. The invention also includes fabricating suture into continuous loops by "threading" at least one suture strand at least partially around the glenoid rim. The suture loops are secured preferably around the periphery of the graft 100 and, as described below, are fastened to bone using bone anchors to hold the graft in place proximate the joint surface being repaired.

As described below, loops 99 will be captured by using devices such as individual forked anchors, for example V-Tak anchors, sold by Arthrex, Inc. of Naples, Fla. and described in U.S. Patent Publ. No 2005/0080455 A1 (the disclosure of which is herein incorporated by reference), allowing attachment of the entire perimeter of the graft to the glenoid. Although FIGS. 4 and 5 illustrate a total of eight loops installed in a pattern similar to that of the drill holes around the glenoid, to match hole placement for anchoring convenience, the invention contemplates any number of loops and corresponding holes formed around the glenoid. If desired, uniformity of each of the individual loops may be provided by tying over a Kelley clamp 93 (FIG. 4), for example, which is utilized as a spacer. Preferably, each loop has a diameter of about 10 to 12 mm. However, the loops may also have various diameters and, depending on the repair site, the loops may need not be uniform. Preferably, each knot corresponding to each loop is 4 throw reverse half hitches for stability. After each loop is tied, the knots may be directed to the back surface of the graft by tugging on the loops gently with a smooth grasper of forceps.

If desired, sutures 96 (FIG. 5), for example #2 FiberWire™, may be additionally employed as traction sutures on the anterior and posterior side of the graft, to aid in the introduction of the graft into the glenohumeral joint. Depending upon the side being operated upon (right versus left), each stitch is placed either above or below the midline of the graft face on its upper edge. Generally, for a left shoulder, the anterior traction stitch is placed at the 10 o'clock area and the posterior stitch is placed at the 4 o'clock area.

According to an exemplary embodiment of the present invention, graft 100 may be soaked or otherwise treated to infuse or coat the graft with platelet rich plasma (PRP), growth factors, medicines, cancer treatments and diagnostic markers, among others. Additionally, biological factors may be introduced to the glenoid repair site prior to aligning the meniscal allograft 100 to the glenoid 20.

To aid in positioning of the graft 100 in relation to the glenoid 20, the superior, anterior and posterior surfaces of the graft as they relate to the humeral head may be marked with an "s," "a" and "p" with a sterile marking pen 60, as shown in FIG. 5.

Referring now to FIG. 6, subsequent to the preparation of the glenoid surface and of the meniscal allograft 100, the allograft is introduced into the glenohumeral joint. The anterior inferior cannula is removed to allow the graft to be passed into the joint. The anterior inferior portal may be extended slightly with a scalpel and then widened with a hemostat, to widen it enough for easy passage of the graft. With the arthroscope in the posterior viewing portal, a passing instrument (for example, an Arthrex SutureLasso) is introduced into the joint through the posterior portal and the wire loop is advanced into the joint. A grasper is utilized through the anterior inferior portal to retrieve the wire loop out of the joint. The posterior #2 FiberWire™ traction sutures 96 (FIGS. 5 and 6) are placed into the wire loop and the loop is pulled back through the joint from anterior to posterior, to lead the graft 100 into the glenohumeral space (FIG. 6). A blunt grasper or hemostat may be utilized to facilitate graft placement into the joint from the anterior portal if the graft interferes with soft tissue during insertion.

Reference is now made to FIGS. 7 and 8. After successful placement of the soft tissue graft 100 on the glenoid 20, the graft is anchored to the glenoid by placing the suture loops 99 in close proximity to the pre-drilled holes 22. The threaded cannula is replaced into the anterior-inferior portal for anchor placement. Suture anchors 50, for example V-Tak anchors, are installed over the loops 99 to attach the perimeter of the graft to the glenoid through the pre-drilled holes 22. Each V-Tak anchor may be introduced into the glenohumeral space through the most convenient portal/cannula and advanced down over suture loop 99, locking the suture loop into the forked tip of the V-Tak (FIG. 7). The V-Tak/suture loop combination is then positioned over the nearest corresponding drill hole 22 and advanced into the hole using a mallet, for example, until the anchor is countersunk just under the cortex and the soft tissue graft properly tensioned to the glenoid without over tensioning it. The steps may be repeated until all available and accessible suture loops 99 have been interfaced with a V-Tak and inserted into their corresponding drill holes 22 to complete the peripheral attachment of the soft tissue graft to the glenoid.

If further reinforcement is necessary, additional sutures may be placed around the labrum and through the upper edge of the soft tissue graft using small diameter cannulated suture passing devices, such as Arthrex Micro Suture Lassos or spinal needles.

Although the present invention has been described above with reference to an exemplary glenoid repair, the invention is not limited to this exemplary embodiment. Those skilled in the art will recognize that the structures and techniques disclosed can be used for joint repair generally. In addition, although the present invention has been described in connection with preferred embodiments, many modifications and variations will become apparent to those skilled in the art. Thus, it is not intended that the present invention be limited to the illustrated embodiments.

What is claimed is:

1. A method of resurfacing a glenoid repair site on a glenoid, comprising:
   securing horns of a meniscal allograft together to form a ring-shaped meniscal allograft;
   installing a plurality of suture loops along the edge of the ring-shaped meniscal allograft to form a ring-shaped meniscal allograft with preattached suture loops;
   forming a plurality of holes on the glenoid rim corresponding to the positions of the suture loops attached to the edge of the ring-shaped meniscal allograft;
   positioning the ring-shaped meniscal allograft with the preattached suture loops to the glenoid repair site so that the suture loops along the edge of the ring-shaped meniscal allograft are aligned with the holes on the glenoid rim; and
   fixing the suture loops to the holes to secure the ring-shaped meniscal allograft to the glenoid.

2. The method of claim 1, wherein the step of fixing the suture loops comprises capturing at least one suture loop using a bone anchor and anchoring the at least one suture loop in the holes.

3. The method of claim 2, wherein the step of anchoring further comprises controlling insertion depth of the bone anchor to obtain proper tensioning of the meniscal allograft.

4. The method of claim 1, further comprising introducing biological factors to the glenoid repair site prior to aligning the meniscal allograft to the glenoid.

5. The method of claim 1, wherein the horns of the meniscal allograft are secured together by using at least one suture strand.

* * * * *